(12) United States Patent
Katsuragawa et al.

(10) Patent No.: US 9,072,635 B2
(45) Date of Patent: Jul. 7, 2015

(54) ABSORBENT ARTICLE

(75) Inventors: Kunihiko Katsuragawa, Kanonji (JP);
Kenichi Sasayama, Kanonji (JP);
Makoto Ichikawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 145 days.

(21) Appl. No.: 13/882,431

(22) PCT Filed: Jan. 25, 2012

(86) PCT No.: PCT/JP2012/000450
§ 371 (c)(1),
(2), (4) Date: Apr. 29, 2013

(87) PCT Pub. No.: WO2012/102034
PCT Pub. Date: Aug. 2, 2012

(65) Prior Publication Data
US 2013/0226119 A1 Aug. 29, 2013

(30) Foreign Application Priority Data
Jan. 27, 2011 (JP) ................................ 2011-015804

(51) Int. Cl.
*A61F 13/535* (2006.01)
*A61F 13/539* (2006.01)
(Continued)

(52) U.S. Cl.
CPC ......... *A61F 13/539* (2013.01); *A61F 13/15658* (2013.01); *A61F 13/4704* (2013.01); *A61F 13/4756* (2013.01); *A61F 13/49001* (2013.01); *A61F 13/5323* (2013.01); *A61F 13/533* (2013.01); *A61F 13/537* (2013.01); *A61F 2013/4587* (2013.01); *A61F 2013/530554* (2013.01); *A61F 2013/530562* (2013.01)

(58) Field of Classification Search
CPC ................ A61F 13/5323; A61F 2013/530562; A61F 2013/530598; A61F 2013/5307; A61F 2013/53051; A61F 2013/530547
See application file for complete search history.

(56) References Cited

U.S. PATENT DOCUMENTS

RE32,957 E * 6/1989 Elias et al. ..................... 604/368
4,935,021 A * 6/1990 Huffman et al. ......... 604/385.26
(Continued)

FOREIGN PATENT DOCUMENTS

| JP | 05038350 A | 2/1993 |
|---|---|---|
| JP | 11099169 A | 4/1999 |

(Continued)

OTHER PUBLICATIONS

English translation of International Search Report and Written Opinion, issued in PCT/JP2012/000450 on Apr. 24, 2012.

*Primary Examiner* — Susan Su
(74) *Attorney, Agent, or Firm* — Lowe Hauptman & Ham, LLP

(57) ABSTRACT

An absorbent article is formed by interposing superabsorbent polymer particles between overlapping two sheets. The pad-shaped absorbent article is composed of superabsorbent polymer particles bonded to the sheet with a hot melt adhesive, absorbing areas where the sheets are not bonded and sealing areas where the sheets are bonded together and surrounding the absorbing areas. Opposed two adjacent bonding areas of the absorbing areas have the sealing areas in between and facing edges which has the sealing areas in between. One of the facing edges is defined by a wavy line having crest and trough portions.

18 Claims, 5 Drawing Sheets

(51) Int. Cl.
    *A61F 13/15*     (2006.01)
    *A61F 13/532*     (2006.01)
    *A61F 13/533*     (2006.01)
    *A61F 13/47*     (2006.01)
    *A61F 13/475*     (2006.01)
    *A61F 13/49*     (2006.01)
    *A61F 13/537*     (2006.01)
    *A61F 13/45*     (2006.01)
    *A61F 13/53*     (2006.01)

(56) References Cited

U.S. PATENT DOCUMENTS

| | | | | |
|---|---|---|---|---|
| 5,149,335 | A | * | 9/1992 | Kellenberger et al. ........ 604/372 |
| 5,411,497 | A | * | 5/1995 | Tanzer et al. ................. 604/368 |
| 5,601,542 | A | * | 2/1997 | Melius et al. ................. 604/368 |
| 5,800,419 | A | * | 9/1998 | Soga et al. .................... 604/368 |
| 5,938,650 | A | * | 8/1999 | Baer et al. ..................... 604/368 |
| 6,610,900 | B1 | * | 8/2003 | Tanzer ........................... 604/368 |
| 8,524,355 | B2 | * | 9/2013 | Nakaoka ........................ 428/198 |
| 2002/0055726 | A1 | * | 5/2002 | Costa ............................. 604/358 |
| 2002/0115969 | A1 | * | 8/2002 | Maeda et al. ................... 604/368 |
| 2006/0184146 | A1 | * | 8/2006 | Suzuki ........................... 604/358 |
| 2007/0093164 | A1 | | 4/2007 | Nakaoka |
| 2007/0135784 | A1 | * | 6/2007 | Tankersley .................... 604/357 |
| 2007/0156107 | A1 | * | 7/2007 | Kimura et al. ................. 604/368 |
| 2007/0197987 | A1 | * | 8/2007 | Tsang et al. ................... 604/365 |
| 2009/0076472 | A1 | * | 3/2009 | Goldwasser et al. ......... 604/365 |
| 2012/0078209 | A1 | * | 3/2012 | Sakai et al. .................... 604/378 |
| 2012/0323195 | A1 | * | 12/2012 | Ehrnsperger et al. ......... 604/366 |
| 2013/0018348 | A1 | * | 1/2013 | Carlucci et al. ............... 604/372 |
| 2013/0226120 | A1 | | 8/2013 | Van De Maele ............... 604/372 |
| 2014/0005625 | A1 | * | 1/2014 | Wirtz et al. .................... 604/372 |

FOREIGN PATENT DOCUMENTS

| | | |
|---|---|---|
| JP | 2001-309941 A | 11/2001 |
| JP | 2004329664 A | 11/2004 |
| JP | 2005287662 A | 10/2005 |
| JP | 2007209786 A | 8/2007 |
| JP | 2009131510 A | 6/2009 |
| JP | 2009-247480 A | 10/2009 |

* cited by examiner

ABSORBENT ARTICLE

RELATED APPLICATIONS

The present application is a National Phase of PCT/2012/000450, filed Jan. 25, 2012, and is based on, and claims priority from, Japanese Application Number 2011-015804, filed Jan. 27, 2011.

TECHNICAL FIELD

The present disclosure relates to absorbent articles, and more specifically, to absorbent articles for bodily fluid absorbent wearing articles such as disposable diapers or disposable wipes.

BACKGROUND OF INVENTION

There are known absorbent articles including superabsorbent polymer particles interposed between two sheet members, at least one of which is liquid permeable.

For example, JP 1993-38350 A (PTL 1) discloses an absorbent sheet provided by, firstly, applying adhesives to an absorbent sheet member, then spreading superabsorbent polymer particles over the sheet member, furthermore overlaying another absorbent sheet member on the sheet member, and finally compressing them all together to form the absorbent sheet.

JP 3732320 B (PTL 2) discloses a disposable wearing article being formed of a liquid permeable top sheet, a liquid impermeable back sheet and a liquid permeable middle sheet underlying beneath the top sheet with a plurality of grooves extending in parallel with each other. The grooves are covered by the top sheet and filled with absorbent materials including superabsorbent polymer particles of 5 to 98 percent by weight.

JP 2009-131510 A (PTL 3) discloses an absorbent sheet including superabsorbent polymer particles interposed between a top sheet and a bottom sheet, and more specifically, in a non-bonded area surrounded by a bonded area where the top sheet and the bottom sheet are bonded together. A pocket is formed between the top sheet and the bottom sheet providing a room for the superabsorbent polymer particles to move freely.

CITATION LIST

Patent Literature

PTL 1: JP 1993-38350 A
PTL 2: JP 3732320 B
PTL 3: JP 2009-131510 A

SUMMARY OF INVENTION

Technical Problem

The inventors have recognized that, the absorbent sheet, disclosed in PTL 1, including two absorbent sheet members and superabsorbent polymer particles interposed between these sheet members, which are bonded together with adhesives, may become less flexible because the superabsorbent polymer particles are uniformly interposed over the entirety between the absorbent sheet members.

The inventors have further recognized that in the absorbent sheet disclosed in PTL 3, the superabsorbent polymer particles relatively freely move before absorbing liquid, so that when the wearing article or the absorbent sheet are used for a disposable diaper, for example, the diaper may not be able to effectively absorb bodily fluid such as urine depending upon the wearer's postures.

Solution to Problem

According to an aspect of the present invention, there is provided an absorbent article having a first direction and a second direction orthogonal to the first direction, including: two sheet members, at least one of which is liquid permeable; and superabsorbent polymer particles interposed between facing surfaces of the two sheet members.

The absorbent article further includes the following features:

one of the facing surfaces of the two sheet members is coated with a first hot melt adhesive;

the superabsorbent polymer particles are bonded to the one of the facing surfaces with the first hot melt adhesive in absorbing areas extending in the second direction and arranged at predetermined intervals in the first direction;

the facing surfaces of the two sheet members are further bonded to each other with a second hot melt adhesive in sealing areas outside the absorbing areas, and the sealing areas are substantially free of the superabsorbent polymer particles;

the absorbing areas adjacent to each other in the first direction have opposite edges by intermediary of the sealing areas, and at least one of the opposite edges is defined by a wavy line having crest portions and trough portions in the second direction.

DESCRIPTION OF EMBODIMENTS

With reference to the drawings attached, absorbent articles in accordance with some embodiments of the present invention will be described in detail hereunder.

Figure 1:
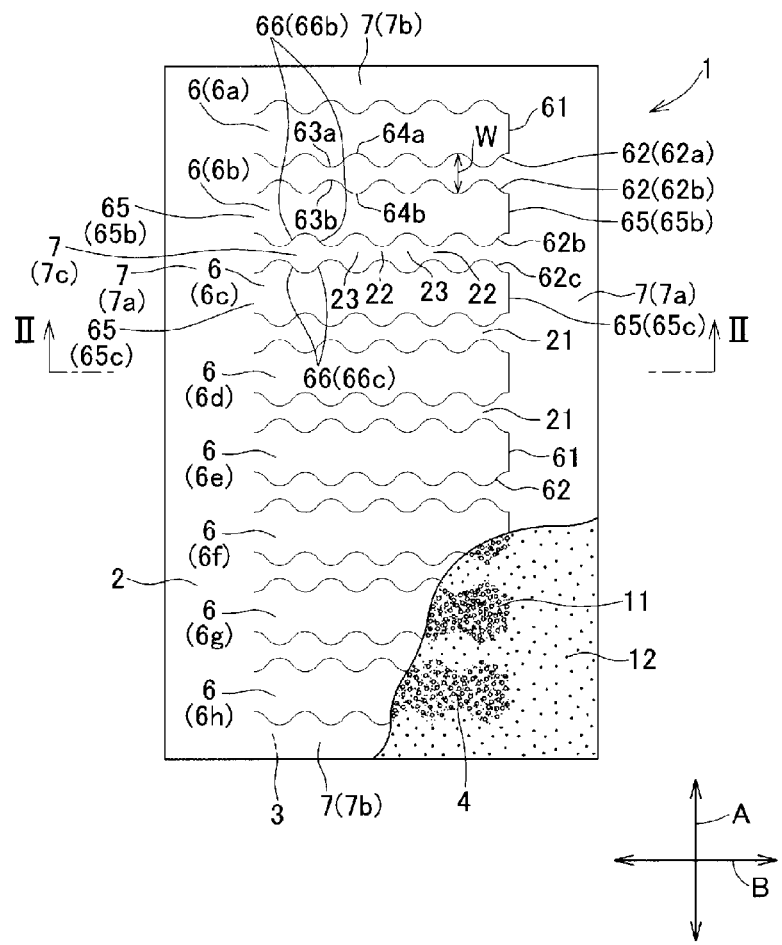
FIG. 1 is a partially cutaway plan view of an absorbent article in accordance with some embodiments.
Figure 2:
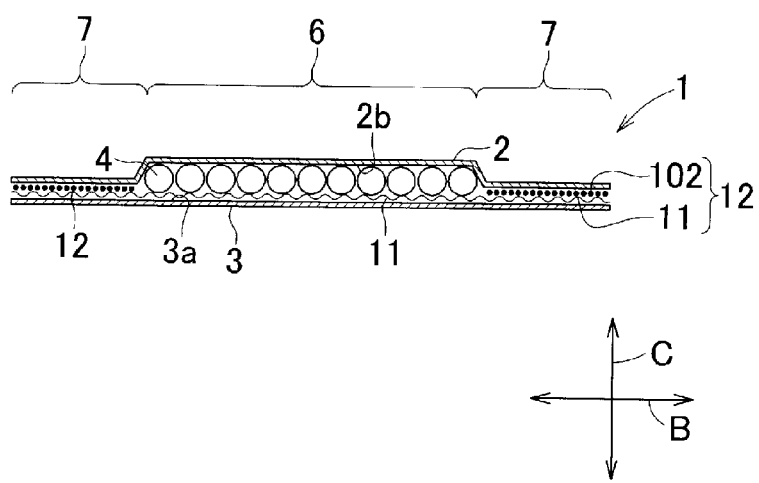
FIG. 2 is a cross sectional view taken along line II-II in FIG. 1.

Referring to FIG. 1 and FIG. 2, double-headed arrows lines A, B and C are orthogonal to each other and show a longitudinal direction, a transverse direction and a thickness direction, respectively, of a pad-shaped absorbent article 1. In these figures, the article 1 has a liquid permeable top sheet 2, a bottom sheet 3, which is either liquid permeable or liquid resistant or liquid impermeable, and superabsorbent polymer particles (hereinafter referred to as "SAP") 4. SAP 4 can be any suitable material known to those skilled in the art or to be developed in the future. A preferable one is a sodium polyacrylate, which is insoluble in water, absorbs more than at least ten times as much water as its own mass. The article 1 includes a plurality of absorbing areas 6 and sealing areas 7 outside the absorbing areas 6. The absorbing areas 6 extend in the transverse direction B and are arranged at predetermined intervals in the longitudinal direction A orthogonal to the transverse direction B. In the absorbing areas 6, the top sheet 2 and the bottom sheet 3 are spaced apart (e.g., substantially free of direct attachment) and SAP 4 sandwiched between those sheets 2 and 3 are bonded to the bottom sheet 3. In the sealing areas 7, the top sheet 2 is bonded to the bottom sheet 3. As used herein, the term "liquid impermeable" with respect to the bottom sheet 3 means that liquid to be absorbed by the absorbent article cannot permeate through the bottom sheet 3. Depending on the situations of actual applications or usages or conditions in production processes of the article 1, any of liquid permeable materials, or liquid resistant materials or liquid impermeable materials may be used for the bottom sheet 3. In FIG. 2, the diameters of SAP 4 are shown on an exaggerated scale in order to show clearly the presence of SAP 4, which will be described hereunder.

The absorbing areas 6 are surrounded by the sealing areas 7 including SAP 4 as an absorbent material, defining an existent area of SAP 4 of a required mass per unit area. In the absorbing areas 6, a mass of SAP 4 from about 30 to about 300 g/m², or more preferably, from about 40 to about 280 g/m², is bonded to the bottom sheet 3 with the hot melt adhesive 11, which are uniformly coated to the entire surface of the bottom sheet 3. The absorbing areas 6 can also accommodate, in some embodiments, some SAP 4 which are not bonded to the bottom sheet 3. The upper limit of the total mass of SAP 4 which the absorbing areas 6 can accommodate between the top sheet 2 and the bottom sheet 3 is about 300 g/m² to about 500 g/m², preferably about 400 g/m². It is preferable that the top sheet 2 and the bottom sheet 3 are not bonded to each other in the absorbing areas 6. However, in the production process of the article 1 (See FIGS. 3, 4), the upper sheet 2, though not intended, may be bonded to the bottom sheet 3 in some very small spots.

The sealing areas 7 are defined along the periphery of each absorbing area 6 to prevent SAP 4 from escaping out of each absorbing area 6, as it may happen when SAP 4 in the absorbing areas 6 are not bonded to the bottom sheet 3 with the hot melt adhesive 11 and are left in a movable state. The sealing areas 7 are substantially non-liquid absorbent and are substantially free of SAP 4, although SAP 4 up to about 20 g/m² may be unintendedly incorporated in the sealing areas 7 during production of the article 1. In the sealing areas 7, the top sheet 2 and the bottom sheet 3 are bonded together with the hot melt adhesive 12, and/or other adhesives. Welding the top sheet 2 and the bottom sheet 3 both of which are already bonded together with the hot melt adhesive 12 may increase peel strength between the sheets 2 and 3. In any case, the top sheet 2 and the bottom sheet 3 in the sealing areas 7 are intended not to be peeled off in use of the article 1. In the article 1 of FIG. 2, the hot melt adhesive 11 and a second hot melt adhesive 102 (See FIG. 4) which will be described later are coated together so as to overlap in the sealing areas 7 and provide the hot melt adhesive 12. The top sheet 2 and the bottom sheet 3 are bonded together with the hot melt adhesive 12. Any hot melt adhesives known in the art or to be developed in the future may be used for the hot melt adhesives 11, 12 and 102.

The article 1 is long in the longitudinal direction A and the absorbing areas 6 include eight (8) individual areas arranged along the longitudinal direction A, each of which is denoted by reference numerals from 6a to 6h and forming a liquid absorbing area containing SAP 4. Each of the individual absorbing areas 6a to 6h has a peripheral edge 61 defining its shape. The peripheral edges 61 of the absorbing areas 6 adjacent to each other in the longitudinal direction A include opposite edges 62 facing each other in the longitudinal direction A and extending laterally in the transverse direction B. For example, in FIG. 1, in the peripheral edges of the absorbing areas 6a, 6b adjacent to each other, the opposite edges 62 facing each other in the longitudinal direction A and extending in the transverse direction B are denoted by reference numerals 62a and 62b. The opposite edges 62a and 62b are undulating in the transverse direction B, which is a lengthwise direction of the opposite edges 62a and 62b. The opposite edges 62a have crest portions 63a and trough portions 64a, respectively, and the opposite edges 62b have crest portions 63b and trough portions 64b, respectively. In the longitudinal direction A, the distance between the opposite portions 63a and 63b is narrower than that between the opposite portions 64a and 64b. In the transverse direction B, a distance of one pitch between a pair of the portions 63b and a distance of one pitch between a pair of the portions 64a are almost the same, and a distance of one pitch between a pair of the portions 64a and a distance of one pitch between a pair of the portions 64b are almost the same.

The sealing area 7 has three portions, i.e., side edge portions 7a positioned on both sides of the article 1 extending in the longitudinal direction A, end portions 7b positioned at both ends of the article 1 and extending in the transverse direction B, and intermediate portions 7c positioned between the absorbing areas 6 adjacent to each other in the longitudinal direction A and extending in the transverse direction B. In other words, each of the intermediate portions 7c is positioned between the opposite edges 62 of the absorbing areas 6 adjacent to each other in the longitudinal direction A and has narrow parts 22 and wide parts 23 measured in the longitudinal direction A.

If the article 1 is applied as an absorbent member for a disposable diaper or as a urine absorbing pad for an incontinence garment, the article 1 is placed on the diaper or the garment in such a manner that the longitudinal direction A of the articles is in line with the front and rear direction of the diaper or the garment and the central portion of the article 1 is laid just over the crotch region of the diaper or the garment. The top sheet 2 is made of a liquid permeable sheet with its surface facing toward the wearer's skin.

The article 1 will provide the diaper (or garment) with one or more various advantages. For example, urine discharged from the wearer will permeate through the top sheet 2 and be absorbed and contained by SAP 4 in the absorbing areas 6 of the article 1 so as not to flow into the diaper. The bonding of SAP 4 to the bottom sheet 3 made of a liquid impermeable sheet and/or a liquid resistant sheet will keep SAP 4 in a uniform distribution, without uneven conglomeration of SAP 4, within the absorbing areas 6 positioned in the wearer's crotch region regardless of the wearer's various postures. Therefore, the article 1 will provide the diaper with a feature that the urine permeates through a broad area of the top sheet 2 and is absorbed and contained over a broad area of each of the absorbing areas 6. In such a diaper, the article 1 will not press the wearer's skin hard by a locally increased thickness of the article 1 brought about by an uneven distribution of SAP 4 within the absorbing areas 6. In the absorbing areas 6 where the hot melt adhesive 11 is coated to the bottom sheet 3, but not coated to the top sheet 2, the hot melt adhesive 11 will not decrease the permeability of the top sheet 2. SAP 4 bonded to the bottom sheet 3 will prevent the top sheet 2 from contacting or being bonded to the bottom sheet 3, to which the hot melt adhesive 11 is coated, and prevent the article 1 from having stiffness brought by the bondage of the top sheet 2 to the bottom sheet 3. A plurality of the intermediate portions 7c will help to make the article 1 positioned in the crotch region of the diaper deform flexibly in the longitudinal direction A. The width W of each intermediate portion 7c as measured in the longitudinal direction A is in a range from about 2 to about 15 mm at the narrow parts 22 and in a range from about 5 to about 20 mm at the wide parts 23. Preferably, the difference in width (W) between the narrow parts 22 and the wide parts 23 is at least 3 mm.

According to an embodiment of the article 1, as the top sheet 2, liquid permeable nonwoven fabrics made of thermoplastic synthetic fibers treated with hydrophilic agents, such as an SMS (spunbond-meltblown-spunbond) nonwoven fabric made of polypropylene fibers treated with hydrophilic agents may be used. As an example of such SMS nonwoven fabrics, there is a sheet material having a basis mass of about 10 to about 12 $g/m^2$, which includes a melt blown nonwoven fabric with a basis mass of about 0.5 to about 2.0 $g/m^2$ interposed between two layers of a spunbond nonwoven fabric with a basis mass of about 4 to about 5 $g/m^2$. Liquid impermeable or liquid resistant nonwoven fabrics made of hydrophobic thermoplastic synthetic fibers are applicable to the bottom sheet 3. For example, sheet materials made of liquid resistant SMS non-fabrics with a basis mass of about 10 to about 13 $g/m^2$ composed of a melt blown fabric with a basis mass of about 0.5 to about 2 $g/m^2$ interposed between two layers of a spunbond nonwoven fabric made of polypropylene fibers with a basis mass of about 4 to about 6 $g/m^2$ is applicable. In addition, for the bottom sheet 3, liquid impermeable sheet members such as a plastic film made from polyethylene with a thickness of about 0.01 to about 0.03 mm, or liquid impermeable sheet members such as a laminate of a liquid permeable or liquid resistant nonwoven fabric made of thermoplastic synthetic fibers and a liquid impermeable plastic film are applicable. In a preferable laminate, SAP 4 are bonded to the nonwoven fabric laid inside the article 1 and the liquid impermeable plastic film is laid outside the article 1 in order to prevent bodily fluid from leaking through the fiber interstices of the nonwoven fabric.

Different kinds of SAP have different liquid absorption speeds. SAP 4 with a single absorption speed or a combination of various absorption speeds may be available for the article 1. For example, SAP 4 with an absorption speed of 30 seconds measured according to the VORTEX method specified by JIS K 7224 may be available with a basis mass of up to about 400 $g/m^2$. It is preferable that the quantity of SAP 4 to be bonded is controlled according to the extent of the area of each absorbing areas 6 or application modes of the article 1. In some embodiments ingredients in SAP 4 that may elute when contacted with urine are included as little as possible. The ingredients eluted from the SAP 4 when contacted with urine may increase viscosity of the urine and may create a discomfort feeling to the wearer, if the urine contacts with the wearer's skin.

The hot melt adhesive 11 is coated to the bottom sheet 3 in the absorbing areas 6 in order to bond SAP 4 to the bottom sheet 3, but in some occasions, the hot melt adhesive 11 may be coated to the sealing areas 7 in the bottom sheet 3. According to FIG. 2, for example, the hot melt adhesive 11 is coated uniformly to the inner surface 3a of the bottom sheet 3 with a basis mass of about 1 to about 12 $g/m^2$. It is preferable that the basis mass of the hot melt adhesive 11 is as low as possible, so that SAP 4, which are to be bonded to the bottom sheet 3 in the absorbing areas 6, are not completely covered with the hot melt adhesive 11. The hot melt adhesive 11 may be coated to the bottom sheet 3 intermittently, for instance, in a dotted pattern or a bead-like pattern, or may be uniformly covering the entire area of the absorbing areas 6. In any case, it is preferable to provide a condition for liquid, such as urine discharged, to be quickly absorbed. For that purpose, in some embodiments, the surfaces of SAP 4 facing the inner surface 3a of the bottom sheet 3 are covered with the hot melt adhesive 11 and bonded to the bottom sheet 3, while the surfaces of SAP 4 facing the inner surface 2b (see FIG. 2) of the top sheet 2 are not covered with the hot melt adhesive 11.

The hot melt adhesive 12 is formed by additionally coating a second hot melt adhesive 102 (in FIG. 4 which will be described hereunder) with a basis mass of about 5 to about 30 $g/m^2$ to the bottom sheet 3 in the sealing areas 7 which is already coated with the hot melt adhesive 11. By controlling the basis mass of the hot melt adhesives in the absorbing areas 6 and the sealing areas 7 in this manner, certain situations in the absorbing areas 6 where the quantity of the liquid to be absorbed and/or the absorption speed of SAP 4 are affected by the hot melt adhesive 11 covering the surface of SAP 4 may be avoided. In the sealing areas 7, if the amount of the hot melt adhesive 11 is not enough to prevent a separation of the top sheet 2 from the bottom sheet 3, e.g., in use, the hot melt adhesive 12 for sealing will contribute to prevent the separation of the two sheets 2, 3. In order to prevent SAP 4 not fixed to the bottom sheet 3 in the absorbing areas 6 from entering the sealing areas 7, it is preferable to coat the hot melt adhesive 12 up to the periphery of the absorbing areas 6 uniformly, or substantially continuously, to secure the top sheet 2 to the bottom sheet 3. The hot melt adhesive 11 and the hot melt adhesive 12 may be of the same materials or different materials, provided that the adhesives are bonded well to each other. If the hot melt adhesive 11 coated to the sealing areas 7 has a sufficient bonding strength to prevent a separation of the two sheets 2, 3 in use, the hot melt adhesive 102 is not required. In this case, the basis mass of the hot melt adhesive will be the same in the absorbing areas 6 and the sealing areas 7.

Plastic films, instead of nonwoven fabrics, may be used for the bottom sheet 3. However, on some occasions, more hot melt adhesive 11 may be required in order to bond SAP 4 to the plastic film. On that occasion, more surface area of SAP 4 tends to be covered with the hot melt adhesive 11.

When the article 1 is applied to a diaper, the dimensions of each absorbing area 6 in the longitudinal direction A and the transverse direction B, in other words, the dimensions of each individual area (e.g., any of individual areas 6a-6h) in the longitudinal direction A and the transverse direction B in FIG. 1 may be suitably decided according to the size of the diaper. For instance, the dimensions for each individual absorbing area can be in a range from about 25 to about 100 mm for the longitudinal direction A and in a range from about 150 to about 250 mm for the transverse direction B, and the number of the absorbing areas 6 are preferably from about 5 to about 15. The width (in the transverse direction B) of the side edge portion 7a and the width (in the longitudinal direction A) of the end portion 7b of the sealing area 7 are preferably in a range from about 5 to about 30 mm.

When the article 1 is applied to a diaper and urine is discharged to the article 1, the intermediate portions 7c of the sealing areas 7 occupying the area between the absorbing areas 6 adjacent to each other may serve as a guiding path of urine in the transverse direction B. However, the guiding path has the narrow part 22 and wide part 23, so the urine flowing into the wide part 23 through the narrow part 22 will flow not only in the transverse direction B but also in the longitudinal direction A as if it is spreading. When the urine flows into the narrow part 22 out of the wide part 23, the width of the urine path is reduced, so that the urine will not flow in the transverse direction B fast enough to reach the side edge portion 7a in the sealing area 7. By forming the liquid guiding path which is non-linear and/or has various widths as exemplarily described, the flowing speed of the urine is decreased and leakage of the urine from the side area of the article 1 may be reduced or prevented. In the wide part 23, the contours of the opposite edges 62 are not straight lines in the transverse direction B, but curved lines, so that, compared with a situation where the opposite edges 62 extend in straight lines in the transverse direction B, SAP 4 kept in individual absorbing areas 6 have more opportunities to encounter with the urine, making the article 1 more effective to absorb and contain the urine. The distance of one pitch between a pair of the portions 63a and the distance of one pitch between a pair of the portions 63b are preferably in a range from about 10 to about 50 mm in the transverse direction B, and both portions 63a, 63b are cooperatively defining the narrow part 22.

In the absorbing areas 6, some of SAP 4 in a swollen state or in a gel-block state brought by the absorption of urine are not fixed to the bottom sheet 3 and will, on some occasions, move relatively freely within the absorbing areas 6. According to a wearer's posture of the diaper, the swollen SAP 4 may move within the absorbing areas 6 in the transverse direction B and, if collected at one or both of the side edges 65 of the absorbing areas 6, may locally increase the thickness of the absorbing areas 6 and may eventually pressing the wearer's skin. However, in the absorbing areas 6 where the contour of opposite edge 62 is defined by a wavy line as shown in FIG. 1, some swollen SAP 4 which move in the transverse direction B along the opposite edges 62 may be stopped in the region 66 (see FIG. 1), because the opposite edges 62 are curved toward the inside of the absorbing areas 6 in a convex pattern so as to make the wide part 23 in the sealing areas 7. Accordingly, even if the wearer is in a state of lying down on the wearer's side, this structure of the article 1 will prevent (or reduce the likelihood of) SAP 4 from moving toward either of the side edges 65 of the absorbing areas 6 and being collected thereat, assuring a uniform distribution of SAP 4 within the absorbing areas 6, in use. In FIG. 1, both side edges 65 of the individual area 6b of the absorbing areas 6 are denoted by a reference numeral 65b and both side edges in another individual area 6c of the absorbing areas 6 is denoted by a reference numeral 65c.

Figure 3:
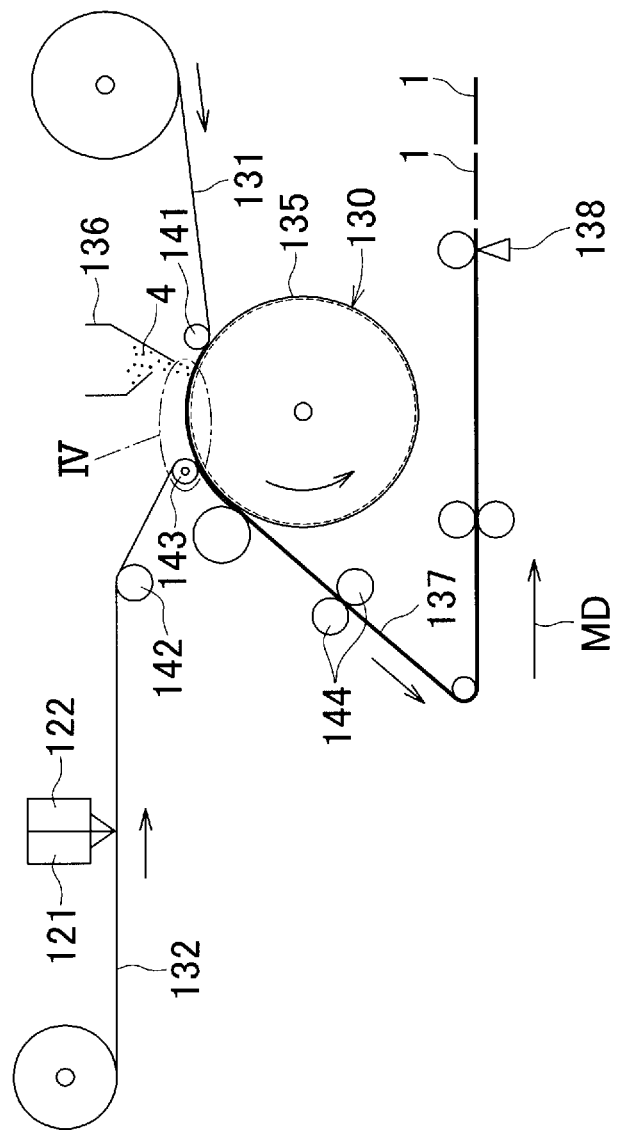
FIG. 3 is an example of a production line for the absorbent article.
Figure 4:
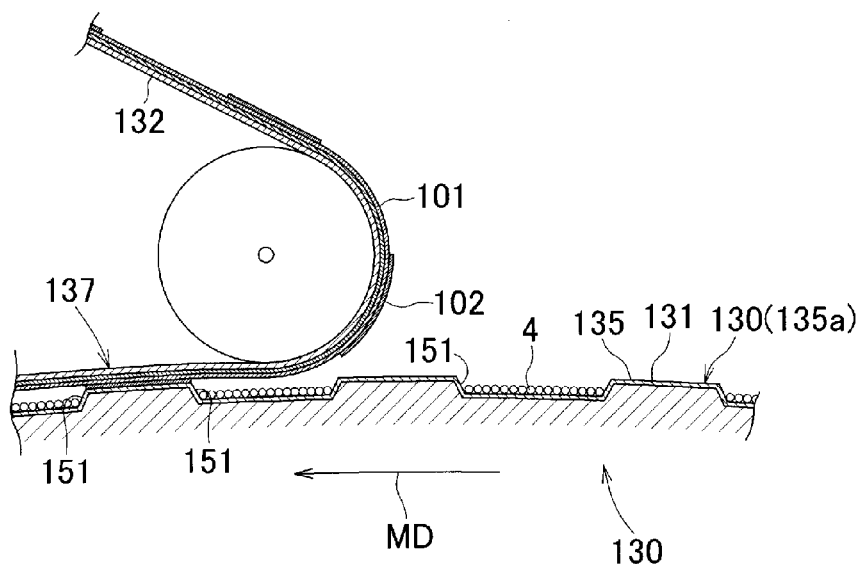
FIG. 4 is an enlarged view of a portion of the production line in FIG. 3.

FIG. 3 and FIG. 4 show a part of a production line of the article 1 and an enlarged view of a suction drum 130 on the production line, respectively. Referring to FIG. 3, a first web 131, which is destined to define the top sheet 2, is continuously fed to the outer surface 135 of the suction drum 130 from the right side of this drawing. SAP applicator 136 located above the suction drum 130 feeds SAP 4 onto the surface of the first web 131, which is in close contact with the outer surface 135 of the suction drum 130 by a suction force exerted inwardly of the suction drum 130 and by a pressing force from a guide roll 141. A second web 132, which is a continuous material of the bottom sheet 3, is continuously fed to the outer surface 135 of the suction drum 130 through guide rolls 142 from the left side of this drawing. One side of the second web 132 is coated with a first hot melt adhesive 101 supplied continuously from a first coater 121 located at a position upstream from the suction drum 130. A second hot melt adhesive 102 is coated to the surface of the web 132, which is already coated with the first hot melt adhesive 101, by a second coater 122 located at a position downstream from the first coater 121. The first web 131 fed with SAP 4 and the second web 132 coated with the first and the second hot melt adhesives 101, 102 are joined together on the outer surface 135 of the suction drum 130 and bonded to form a composite web 137. The composite web 137 is cut into a size of the article 1 by a cutting machine 138 at predetermined intervals. A portion of the first hot melt adhesive 101 is destined to define the hot melt adhesive 11 in the article 1, and another portion of the first hot melt adhesive 101 cooperates with the second hot melt adhesive 102 to provide the hot melt adhesive 12 for sealing. Details of the production process where the composite web 137 is formed are illustrated in FIG. 4.

FIG. 4 illustrates cross sectional views of the first web 131 and the second web 132 both of which are joined together to form the composite web 137. A plurality of concave regions 151 are arranged circumferentially on the outer surface 135 of the suction drum 130. Each of the concave regions 151 in a plan view corresponds to the individual absorbing areas of the absorbing areas 6 arranged in the longitudinal direction A as shown in FIG. 1. The depth of the concave region 151 is configured to let each concave region 151 have a volume large enough to deposit a quantity of one-time feed of SAP 4 fed intermittently from the polymer SAP applicator 136. The first web 131 in contact with the outer surface 135 of the suction drum 130 is deformed by the suction force of the suction drum 130 working inwardly so as to conform to the inner shape of the concave region 151. SAP 4 fed from SAP applicator 136 is deposited in the deformed portion of the first web 131. Between the adjacent concave regions 151 on the outer surface 135, a convex region 135a is formed. When the first web 131 and the second web 132 are joined together and run through between the first press roll 143 and the convex region 135a of the outer surface 135, the first web 131 and the second web 132 are compressed by the first press roll 143 and the convex region 135a, providing the composite web 137. After having left from the suction drum 130 in the machine direction MD, the composite web 137 is compressed by a pair of second press rolls 144 (FIG. 3), making SAP 4 contacted with the first hot melt adhesive 101 and bonding SAP 4 to the second web 132 with the first hot melt adhesive 101. Referring to FIG. 3, the composite web 137 advances to a clearance between the pair of the second press rolls 144 at a slanted angle against the MD direction shown with a horizontal arrow line, but preferably the composite web 137 is conveyed into the clearance between the pair of the second press rolls 144 almost horizontally to make sure a horizontally uniform distribution of SAP 4 within a space between the first web 131 and the second web 132.

In the article 1 formed in this manner, the first hot melt adhesive 101 can be coated uniformly or intermittently either in the longitudinal direction A or in the transverse direction B of each of the absorbing areas 6 and the sealing areas 7, or can be coated continuously at least in either of the longitudinal direction A or the transverse direction B of the article 1. Therefore, there are no special requirements for the selection of the first coater 121 for the first hot melt adhesive 101, and the same applies to the second coater 122 for the second hot melt adhesive 102. It is preferable that the hot melt adhesive 11 in the absorbing areas 6 and the hot melt adhesive 12 in the sealing area 7 are coated in the article 1 in such a manner that each of the adhesives 11, 12 is contiguous, or the adhesives 11, 12 are positioned within a distance of less than 5 mm. When the hot melt adhesive 11 is coated in such a manner and pervading through the entire area of each absorbing area 6 including its four corners of the absorbing area 6, SAP 4 will also be pervading through the entire area of each absorbing area 6 as well. For instance, SAP 4 can be aligned just inside the opposite edges 62 and distributed uniformly along the opposite edges 62 of each absorbing area 6. It is preferable that SAP 4 is distributed to cover almost the entire area of the inner surface 3a of the bottom sheet 3 in each absorbing areas 6, so that SAP 4 can prevent the top sheet 2 from being bonded to the bottom sheet 3 with the hot melt adhesive 11 in the absorbing areas 6.

It is also preferable that all of SAP 4 are bonded to the inner surface 3a of the bottom sheet 3 in the absorbing areas 6. Even if, however, some of SAP 4 are not bonded to the bottom sheet 3 and free to move in a space between the bottom sheet 3 and the top sheet 2 of the absorbing areas 6, one or more of the advantages and/or the objectives disclosed herein may be achieved. In order to hold SAP 4 within the absorbing areas 6 in such a condition as described above, it is preferable that the top sheet 2 and the bottom sheet 3, if made of nonwoven fabrics, have a structure that SAP 4 will not easily enter the fiber interstices of the nonwoven fabrics or pass through the interstices. Accordingly, the nonwoven fabrics for the top sheet 2 or the bottom sheet 3 are selected from such nonwoven fabrics which do not allow SAP 4 to enter the fiber interstices of the nonwoven fabrics when SAP 4 are dispersed over the nonwoven fabrics which are under a vibration. There are no specific requirements for a shape of the article 1 or a shape of the absorbing areas 6 or the number of the individual areas of the absorbing areas 6, so that suitable modifications in the shape and/or the number of the individual areas of the absorbing areas 6 will be allowed. For instance, the shape of each of the sealing areas 7 may be changed so as to divide each of the individual areas (e.g., 6a-6h) into two or more sub-areas arranged intermittently in the transverse direction B.

It is also possible to use SAP 4 blended with a second superabsorbent polymer particles (not shown) having a different absorption speed from that of SAP 4 in the absorbing areas 6. For instance, SAP 4 bonded to the bottom sheet 3 having an absorption speed $AS_1$ of 3 seconds measured by the VORTEX method and the second superabsorbent polymer particles having an absorption speed $AS_2$ of 30 seconds measured by the VORTEX method can be used together. The second superabsorbent polymer particles can be bonded to the upper sheet 2 with a third hot melt adhesive (not shown) in the absorbing areas 6, or can be bonded to neither of the top sheet 2 nor the bottom sheet 3 and left in the absorbing areas 6 in a freely movable condition. SAP 4 with a faster absorption speed $AS_1$ can be located near the bottom sheet 3 and the second superabsorbent polymer particles with a slower absorption speed $AS_2$ can be located adjacent to the top sheet 2 in the article 1. When the diaper having the article 1 described above is worn with the top sheet 2 facing the wearer's skin, the urine discharged in the beginning may be absorbed by SAP 4 located far from the wearer's skin and retained there apart from the skin before gel blocks are formed by the second absorbent polymer particles, and the urine discharged afterward can be absorbed by the second superabsorbent polymer particles located adjacent to the wearer's skin, so that the wearer of the diaper having this article 1 may be relieved of an uncomfortable wearing condition brought by dampness of the article 1. Preferably, the combined basis mass of SAP 4 and the second superabsorbent polymer particles in the absorbing areas 6 does not exceed about 400 g/m$^2$.

Figure 5:
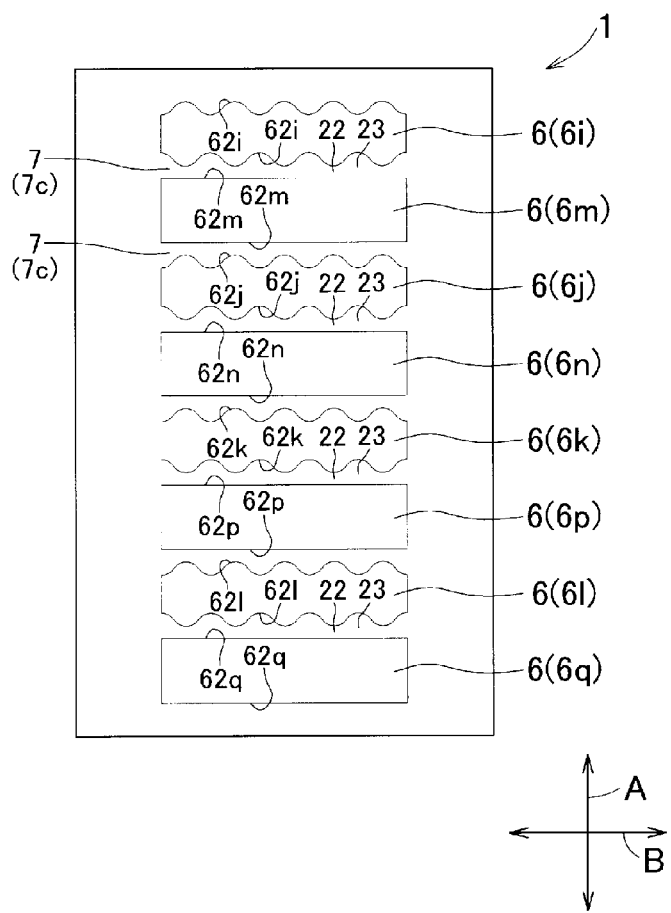
FIG. 5 is a view similar to FIG. 1 showing an embodiment of the present invention.

FIG. 5 is a plan view similar to FIG. 1 (but without a partially cut away portion), and shows the article 1 in accordance with an embodiment. The absorbing areas 6 in the article 1 in FIG. 5 have individual absorbing areas 6i, 6j, 6k, 6l similar in shape to the individual areas 6a to 6h of the absorbing areas 6 in FIG. 1, and individual absorbing areas 6m, 6n, 6p, 6q having rectangular shapes. The individual absorbing areas 6i, 6j, 6k, 6l respectively have opposite wavy edges 62i, 62j, 62k, 62l extending in the transverse direction B. The individual absorbing areas 6m, 6n, 6p, 6q respectively have opposite straight edges 62m, 62n, 62p, 62q extending in the transverse direction B. In the intermediate portions 7c of the sealing areas 7, the narrow part 22 and the wide part 23 are formed. The article 1 of this structure also works in a manner similar to that of the article 1 in FIG. 1.

Figure 6:
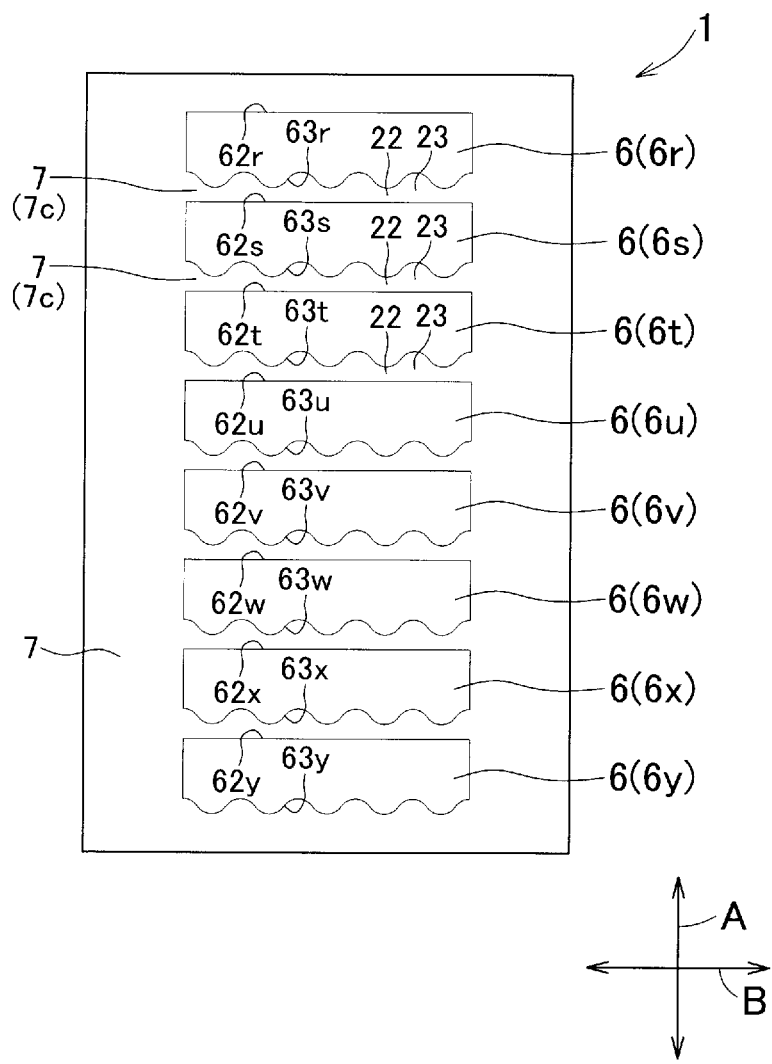
FIG. 6 is a view similar to FIG. 5 showing an embodiment of the present invention.

FIG. 6 is a plan view of the article 1, in accordance with another embodiment, similar to that in FIG. 5, but all of the individual areas 6r, 6s, 6t, 6u, 6v, 6w, 6x, 6y of the absorbing areas 6 are in the same shape. One of the opposite edges 62 is straight and denoted by 62r, 62s, 62t, 62u, 62v, 62w, 62x, 62y corresponding to each of the individual areas, while the other of the opposite edges 62 is wavy and denoted by 63r, 63s, 63t, 63u, 63v, 63w, 63x, 63y which extend in the transverse direction B. This article 1 also has the narrow part 22 and the wide part 23 in the intermediate zones 7c. The article 1 of this structure also works in a manner similar to those of the articles 1 in FIG. 1 and FIG. 5.

Figure 7:
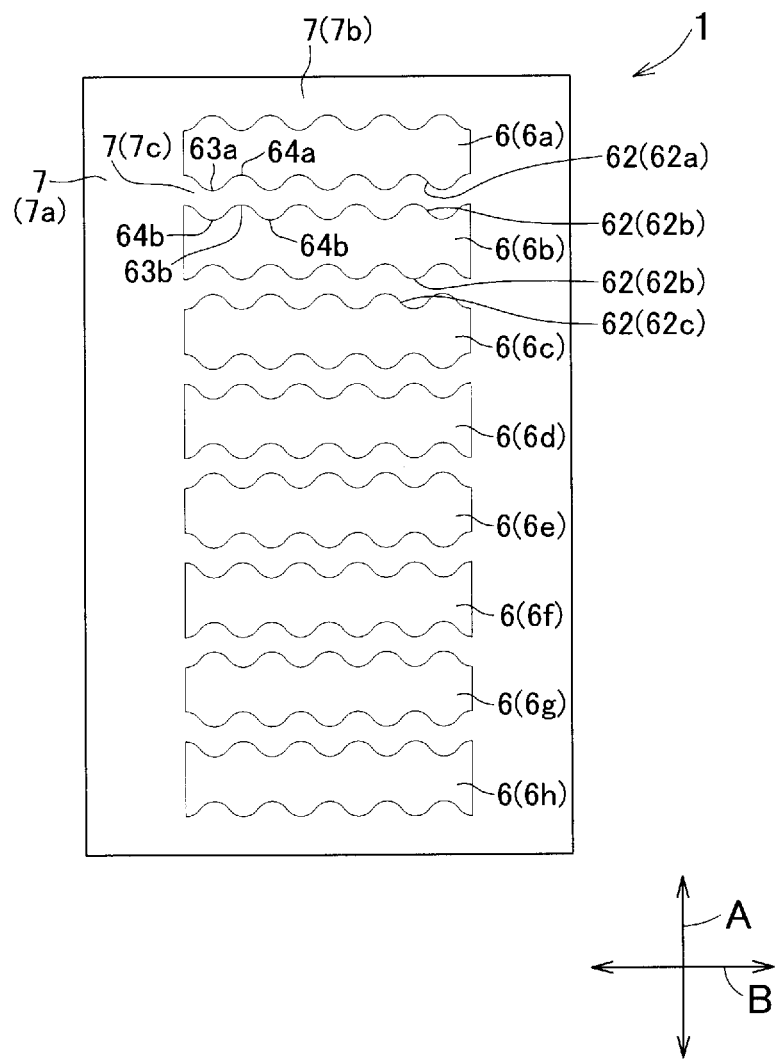
FIG. 7 is a view similar to FIG. 1 showing another embodiment of the present invention.

FIG. 7 is a plan view similar to FIG. 1 (but without a partially cut away portion), and shows the article 1 in accordance with another embodiment. The article 1 in FIG. 7 has the individual areas of the absorbing areas 6, which are denoted by reference numerals 6a to 6h. Each of the individual areas 6a to 6h has opposite edges 62. Each of the opposite edges 62 extends in the transverse direction B in a wavy line, having the portions 63 and 64 on the opposite edges 62. Between a pair of adjacent individual areas, the crest portion 63 of one individual area faces the trough portion 64 of the other individual area, likewise, the trough portion 64 of the one individual area faces the crest portion 63 of the other individual area. The intermediate portions 7c of the sealing area 7 located between the opposite edges 62 of the adjacent individual areas extend respectively in the transverse direction B in wavy lines. The situations described above will be described hereunder with the individual absorbing areas 6a and 6b of the absorbing areas 6. The absorbing areas 6 have the individual absorbing area 6a which has the opposite edges 62a, on at least one of which are positioned the crest portions 63a and the trough portions 64a. The absorbing areas 6 have similarly the individual absorbing areas 6b which has opposite edges 62b, on at least one of which are positioned the crest portions 63b and a trough portions 64b. Regarding the opposite edges 62a and 62b, the crest portions 63a on the opposite edge line 62a faces the trough portions 64b on the other opposite edge line 62b, and the trough portions 64a on the opposite edge line 62a faces the crest portion 63b on the other opposite edge 62b.

The article 1 having such opposite edges 62 as exemplified by the opposite edges 62a and 62b shown in FIG. 7 has the intermediate portions 7c waving in the sealing areas 7. Owing to the waving intermediate portions 7c, the urine discharged will not flow quickly in the transverse direction B, and the length of the path for the urine to flow will be extended compared to that of a straight line. Therefore, the urine will have more opportunities to contact with SAP 4, and thus sideway leakage of urine from the diaper will be reduced or prevented. If there are SAP 4 which are in a state of being not bonded to the bottom sheet 3 or the top sheet 2, and in a swollen or gel-blocking state, the opposite edges 62 will contribute to prevent (or reduce the likelihood of) SAP 4 in such a state from gathering to one side 65 (see FIG. 1) of the absorbing area 6 and help to disperse SAP 4 in a broader area in the absorbing areas 6.

The application of the article 1 is not limited to a disposable diaper, but to any product where liquid absorbency is desirable. For example, the article 1 may be applicable to a urine absorbent pad to be coupled with a diaper or a diaper cover, or a urine absorbent pad to be coupled with an underwear or a garment for incontinent persons. The article 1 is also applicable to wipes which are used for absorbing liquid such as waste water, or other water absorbent articles. When the article 1 is used as the wipes, liquid permeable or liquid impermeable or liquid resistant sheets may be used for the bottom sheet 3 of the article 1.

(1) An aspect of the present invention may be arranged in at least the following features:

The absorbent article having a first direction and a second direction orthogonal to the first direction, includes:

two sheet members, at least one of which is liquid permeable; and superabsorbent polymer particles interposed between facing surfaces of the two sheet members;

wherein one of the facing surfaces of the two sheet members is coated with a first hot melt adhesive;

the superabsorbent polymer particles are bonded to the one of the facing surfaces with the first hot melt adhesive in absorbing areas extending in the second direction and arranged at predetermined intervals in the first direction;

the facing surfaces of the two sheet members are further bonded to each other with a second hot melt adhesive in sealing areas outside the absorbing areas, and the sealing areas are substantially free of the superabsorbent polymer particles;

the absorbing areas adjacent to each other in the first direction have opposite edges by intermediary of the sealing areas, and at least one of the opposite edges is defined by a wavy line having crest portions and trough portions in the second direction.

(2) The aspect of the present invention described in (1) may include at least the following embodiments:

(i) The crest and trough portions of one of the opposite edges of the absorbing areas adjacent to each other in the first direction respectively face the crest and trough portions of the other of the opposite edges of the absorbing areas adjacent to each other in the first direction.

(ii) The other of the opposite edges is defined by a straight line.

(iii) The crest and trough portions of one of the opposite edges of the absorbing areas adjacent to each other in the first direction respectively face the trough and crest portions of the other of the opposite edges of the absorbing areas adjacent to each other in the first direction.

(iv) Each of the two sheet members is liquid permeable.

(v) One of the two sheet members is liquid permeable and the other of the two sheet members is either liquid impermeable or liquid resistant, and the superabsorbent polymer particles are bonded to the other of the two sheet members.

(vi) The two sheet members are a hydrophilic nonwoven fabric made of thermoplastic synthetic fibers.

(vii) The liquid impermeable or liquid resistant sheet member is one of (a) a hydrophobic nonwoven fabric made of thermoplastic synthetic fibers and (b) a laminate of the hydrophobic nonwoven fabric and a liquid impermeable plastic film, and the superabsorbent polymer particles are bonded to the hydrophobic nonwoven fabric.

(viii) The first hot melt adhesive and the second hot melt adhesive are contiguous.

(ix) The first hot melt adhesive and the second hot melt adhesive are adjacent to each other.

(x) The superabsorbent polymer particles have an absorption speed of $AS_1$ and second absorbent polymer particles with a lower absorption speed of $AS_2$ than $AS_1$ are interposed between the two sheet members in the absorbing areas.

(xi) The second superabsorbent polymer particles are bonded to the other one of the facing surfaces with a further hot melt adhesive.

(xii) The second superabsorbent polymer particles are not bonded to either of the facing surfaces.

(xiii) The first hot melt adhesive for bonding the superabsorbent polymer particles in the absorbing areas is the same as the second hot melt adhesive in the sealing areas.

(xiv) The first direction corresponds to a longitudinal direction of the article and the second direction corresponds to a transverse direction of the article.

(3) Another aspect of the present invention may be arranged in at least the following features:

An absorbent article having a first direction and a second direction orthogonal to the first direction, includes:

two sheet members, at least one of which is liquid permeable; and superabsorbent polymer particles interposed between facing surfaces of the two sheet members;

wherein the superabsorbent polymer particles are adhesively bonded to one of the facing surfaces in absorbing areas extending in the second direction and arranged at predetermined intervals in the first direction;

the facing surfaces of the two sheet members are further adhesively bonded to each other in sealing areas outside the absorbing areas, and the sealing areas are substantially free of the superabsorbent polymer particles;

the sealing areas include an intermediate portion positioned between the absorbing areas adjacent to each other in the first direction, the intermediate portion defining a guiding path for liquid discharged on the article in the second direction, the path being non-linear or having various widths for reducing a speed of the liquid flowing on the path.

(4) The aspect of the present invention described in (3) may include at least the following embodiments:

(i) The liquid guiding path is defined by opposite edges of the absorbing areas adjacent to each other in the first direction, at least one of the opposite edges being a wavy line.

(ii) The other of the opposite edges is a straight line.

(iii) The liquid guiding path is defined by opposite edges of the absorbing areas adjacent to each other in the first direction, each of the opposite edges being a wavy line having at least one crest portion and at least one trough portion, and the crest and trough portions of one of the opposite edges respectively face the crest and trough portions of the other of the opposite edges.

(iv) The liquid guiding path is defined by opposite edges of the absorbing areas adjacent to each other in the first direction, each of the opposite edges being a wavy line having at least one crest portion and at least one trough portion, and the crest and trough portions of one of the opposite edges respectively face the trough and crest portions of the other of the opposite edges.

The described aspects and/or embodiments provide one or more of the following effects.

In a pad-shaped absorbent article disclosed in the present invention, the sheet members are sealed to each other in sealing areas, while in the absorbing areas, the superabsorbent polymer particles located between the sheet members will serve to prevent the sheet members from being directly bonded to each other. Accordingly, a problem of decrease in flexibility of the absorbent article will be solved and the absorbent article will be flexible. The superabsorbent polymer particles are bonded to either one of the opposed sheet members in the absorbing areas, so that the superabsorbent polymer particles may be uniformly distributed within the absorbing areas independent of the wearer's postures of the absorbent article. At least one of the opposite edges in the absorbing areas is defined in the wavy line having the crest and trough portions, so that even if some of the superabsorbent polymer particles are released from bonded states in the absorbing areas, the polymer particles will not move freely along one of the opposite edges toward the first direction due to the crest and trough patterns.

This application claims the benefit of Japanese Application No. 2011-15804 the entire disclosure of which is incorporated by reference herein.

The invention claimed is:

1. An absorbent article having a first direction and a second direction orthogonal to the first direction, said absorbent article comprising:
   two sheet members, at least one of which is liquid permeable; and
   superabsorbent polymer particles interposed between facing surfaces of the two sheet members;
   wherein
   one of the facing surfaces of the two sheet members is coated with a first hot melt adhesive,
   the superabsorbent polymer particles are bonded to the one of the facing surfaces with the first hot melt adhesive in absorbing areas extending in the second direction and arranged at predetermined intervals in the first direction,
   the facing surfaces of the two sheet members are further bonded to each other with a second hot melt adhesive in sealing areas outside the absorbing areas, and the sealing areas are substantially free of the superabsorbent polymer particles,
   the absorbing areas adjacent to each other in the first direction have opposite edges by intermediary of the sealing areas, and at least one of the opposite edges is defined by a wavy line having crest portions and trough portions in the second direction,
   the superabsorbent polymer particles have an absorption speed of $AS_1$,
   second superabsorbent polymer particles having an absorption speed of $AS_2$ lower than the absorption speed of $AS_1$ are interposed between the two sheet members in the absorbing areas, and
   the second superabsorbent polymer particles are bonded to the other one of the facing surfaces with a further hot melt adhesive.

2. The article defined by claim 1, wherein the crest and trough portions of one of the opposite edges of the absorbing areas adjacent to each other in the first direction respectively face the crest and trough portions of the other of the opposite edges of the absorbing areas adjacent to each other in the first direction.

3. The article defined by claim 1, wherein the other of the opposite edges is defined by a straight line.

4. The article defined by claim 1, wherein the crest and trough portions of one of the opposite edges of the absorbing areas adjacent to each other in the first direction respectively face the trough and crest portions of the other of the opposite edges of the absorbing areas adjacent to each other in the first direction.

5. The article defined by claim 1, wherein each of the two sheet members is liquid permeable.

6. The article defined by claim 1, wherein
   one of the two sheet members is liquid permeable and the other of the two sheet members is either liquid impermeable or liquid resistant, and
   the superabsorbent polymer particles are bonded to the other of the two sheet members.

7. The article defined by claim 6, wherein
   the liquid impermeable or liquid resistant sheet member is one of (a) a hydrophobic nonwoven fabric made of thermoplastic synthetic fibers and (b) a laminate of the hydrophobic nonwoven fabric and a liquid impermeable plastic film, and
   the superabsorbent polymer particles are bonded to the hydrophobic nonwoven fabric.

8. The article defined by claim 1, wherein the two sheet members are hydrophilic nonwoven fabrics made of thermoplastic synthetic fibers.

9. The article defined by claim 1, wherein the first hot melt adhesive and the second hot melt adhesive are contiguous.

10. The article defined by claim 9, wherein the first hot melt adhesive for bonding the superabsorbent polymer particles in the absorbing areas is the same as the second hot melt adhesive in the sealing areas.

11. The article defined by claim 1, wherein the first hot melt adhesive and the second hot melt adhesive are adjacent to each other.

12. The article defined by claim 1, wherein the first direction corresponds to a longitudinal direction of the article and the second direction corresponds to a transverse direction of the article.

13. The article defined by claim 1, wherein
    the sealing areas include an intermediate portion positioned between the absorbing areas adjacent to each other in the first direction, the intermediate portion defining a guiding path for liquid discharged on the article in the second direction, the path being non-linear or having various widths for reducing a speed of the liquid flowing on the path.

14. The article defined by claim 13, wherein the liquid guiding path is defined by the opposite edges of the absorbing areas adjacent to each other in the first direction.

15. The article defined by claim 14, wherein the other of the opposite edges is a straight line.

16. The article defined by claim 13, wherein
    the liquid guiding path is defined by the opposite edges of the absorbing areas adjacent to each other in the first direction, each of the opposite edges being a wavy line having at least one crest portion and at least one trough portion, and
    the crest and trough portions of one of the opposite edges respectively face the crest and trough portions of the other of the opposite edges.

17. The article defined by claim 13, wherein
    the liquid guiding path is defined by the opposite edges of the absorbing areas adjacent to each other in the first direction, each of the opposite edges being a wavy line having at least one crest portion and at least one trough portion, and
    the crest and trough portions of one of the opposite edges respectively face the trough and crest portions of the other of the opposite edges.

18. An absorbent article having a first direction and a second direction orthogonal to the first direction, said absorbent article comprising:
    two sheet members, at least one of which is liquid permeable; and
    superabsorbent polymer particles interposed between facing surfaces of the two sheet members;
    wherein
    one of the facing surfaces of the two sheet members is coated with a first hot melt adhesive,
    the superabsorbent polymer particles are bonded to the one of the facing surfaces with the first hot melt adhesive in absorbing areas extending in the second direction and arranged at predetermined intervals in the first direction, the facing surfaces of the two sheet members are further bonded to each other with a second hot melt adhesive in sealing areas outside the absorbing areas, and the sealing areas are substantially free of the superabsorbent polymer particles, the absorbing areas adjacent to each other in the first direction have opposite edges by intermediary of the sealing areas, and at least one of the opposite edges is defined by a wavy line having crest portions and trough portions in the second direction, the superabsorbent polymer particles have an absorption speed of $AS_1$, second superabsorbent polymer particles having an absorption speed of $AS_2$ lower than the absorption speed of $AS_1$ are interposed between the two sheet members in the absorbing areas, and the second superabsorbent polymer particles are not bonded to either of the facing surfaces.

* * * * *